United States Patent [19]

Edwards, Jr.

[11] Patent Number: 5,366,736
[45] Date of Patent: Nov. 22, 1994

[54] VITAMIN D DERIVATIVE FEED COMPOSITIONS AND METHODS OF USE

[75] Inventor: Hardy M. Edwards, Jr., Winterville, Ga.

[73] Assignee: University of Georgia Research Foundation, Inc., Athens, Ga.

[21] Appl. No.: 103,904

[22] Filed: Aug. 10, 1993

Related U.S. Application Data

[63] Continuation of Ser. No. 861,109, Mar. 31, 1992, Pat. No. 5,316,770, which is a continuation-in-part of Ser. No. 630,748, Dec. 20, 1990, Pat. No. 5,154,925, which is a continuation of Ser. No. 311,540, Feb. 16, 1989, abandoned.

[51] Int. Cl.$^5$ ............................................. A61K 31/59
[52] U.S. Cl. .................................. 424/442; 424/94.1; 426/2; 426/73; 514/167
[58] Field of Search ........................ 424/442; 514/167

[56] References Cited

U.S. PATENT DOCUMENTS

5,043,170 8/1991 Borenstein et al. ................. 426/73

Primary Examiner—Thurman K. Page
Assistant Examiner—James M. Spear
Attorney, Agent, or Firm—Kilpatrick & Cody

[57] ABSTRACT

Methods and compositions for enhancement of phytate phosphorus utilization and treatment and prevention of tibial dyschondroplasia in animals, particularly poultry, by administering to animals a feed composition containing a hydroxylated vitamin $D_3$ derivative. The vitamin $D_3$ derivative is preferably administered to animals in feed containing reduced levels of calcium and phosphorus for enhancement of phytate phosphorus utilization. The vitamin $D_3$ derivative is administered in combination with active phytase for further enhancement of phytate phosphorus utilization, 20 Claims, 3 Drawing Sheets

VITAMIN D DERIVATIVE FEED COMPOSITIONS AND METHODS OF USE

CROSS-REFERENCE TO RELATED APPLICATIONS

This a continuation of U.S. Ser. No. 07/861,109 filed on Mar. 31, 1992, U.S. Pat. No. 5,316,770 which is a continuation-in-part of U.S. patent application Ser. No. 07/630,748, U.S. Pat. No. 5,154,925, to Hardy Malcolm Edwards, Jr., for Treatment of Tribial Dyschondroplasia, filed Dec. 20, 1990, which is a continuation of U.S. patent application Ser. No. 07/311,540, filed Feb. 16, 1989, now abandoned.

BACKGROUND OF THE INVENTION

This invention relates to the field of biochemistry, and more particularly relates to animal feed compositions.

Phytate Phosphorus Utilization

Animals, including humans, require phosphorus in their diets for proper growth and health. Farm animals are normally fed a grain-based animal feed. Most of these grain-based feeds contain from 50-80% of their total phosphorus as phytate phosphorus. Phytate phosphorus in plants occurs as the mixed calcium-magnesium-potassium salt of the organic compound, phytic acid.

Many animals are unable to utilize most of the phytate phosphorus they receive in their feed. For example, studies by Edwards and Veltmann, *J. Nutr.* 113:1268–1575 (1983) and Ballam et al., *Poultry Sci.* 63:333–338 (1984) with young broiler chickens fed corn-soybean diets indicate phytate phosphorus utilization of from only 10 to 53%. Feed consumed by these animals must be supplemented with inorganic phosphorus, such as in the form of dicalcium phosphate or defluorinated phosphate. The cost of phosphorus supplementation is high. In addition, the unused phytate phosphorus is excreted, creating phosphorus soil contamination and costly ecological problems.

The mechanisms involved in phytate phosphorus utilization by animals are unknown. Utilization of phytate phosphorus by chickens has been reviewed by several scientists including T. S. Nelson, *Poultry Sci.* 46:862–871 (1967). Phytate phosphorus utilization in broiler chickens has been shown by Edwards et al., *Poultry Sci.* 67:1436–1446 (1988) to be influenced by age. Other scientists, such as Lowe and Steenbock, *Biochem J.* 30:1992–1995 (1936), Common, *Agric. Sci.* 30:113–131 (1940), Edwards and Veltmann, *J. Nutr.* 113:1268-1575 (1983), Ballam et al., *Poultry Sci.* 63:333–338 (1984) and Sooncharernying and Edwards, *Poultry Sci.* 69(Suppl. 1):129 (1990), have shown that phytate phosphorus utilization may be influenced by calcium, phosphorus, and aluminum levels in the diet.

A method that would increase phytate phosphorus utilization by animals, especially farm animals such as chickens, would reduce the costs of raising such animals because phosphate supplementation would be unnecessary. In addition, the soaring costs associated with the decontamination of soil containing elevated phosphates would be greatly reduced or even eliminated.

Tibial Dyschondroplasia

Tibial dyschondroplasia is a skeletal abnormality which occurs in rapidly growing animals such as broiler chickens or turkeys. The cause of tibial dyschondroplasia is unknown. Tibial dyschondroplasia is distinguished from rickets, a vitamin D deficiency disease characterized by overproduction and deficient calcification of osteoid tissue, in that a high incidence of tibial dyschondroplasia is found in animals that receive a sufficient dietary supply of vitamin D and are adequately exposed to sunlight.

Tibial dyschondroplasia is characterized by an unmineralized, unvascularized mass of cartilage located in the proximal ends of the tibiotarsus and the tarsusmetatarsus. The cartilage extends from the growth plate into the metaphysis. In fowl, tibial dyschondroplasia usually appears between three and eight weeks of age. In some chickens and turkeys, the prehypertrophic cartilage persists into adulthood but is restricted to the posterior medial portion of the proximal tibiotarsal bone so that the birds remain clinically normal. An incidence of 10 to 30% of birds with subclinical dyschondroplasia is common in many flocks. In the more severe cases of tibial dyschondroplasia, the abnormal tissue occupies the whole metaphysis of the proximal tibiotarsal bone and also develops in the proximal tarsometatarsal bone.

Birds with these more severe lesions may be lame, with bowing of the affected bones. These chickens are unable to walk normally and often collapse, causing injury and decreasing growth rate. The disease also increases the death rate of animals during the growth period. Further, many of the birds suffering from tibial dyschondroplasia develop breast blisters and leg deformities that result in hemorrhages.

Tibial dyschondroplasia increases the percentage of carcasses that must be downgraded or condemned during processing, resulting in decreased profits for the processor. The deformed legs of birds with tibial dyschondroplasia often interfere with the shackling of the fowl during processing and can actually cause mechanical problems in operating the processing line where the slaughtered fowl are conveyed on machines which handle the birds by their legs. Fowl with tibial dyschondroplasia have insufficient leg strength to be carried in this manner.

A number of studies have been conducted to determine both the cause of dyschondroplasia and a method for treatment or prevention. Leach and Nesheim, "Further Studies on Tibial Dyschondroplasia Cartilage Abnormality in Young Chicks",*J. Nutr.* 102:1673 (1972), indicated that the cartilage abnormality is a result of an inherited physiological defect, the expression of which is under dietary control. They were not able to determine the nutritional factors responsible for expression. However, they found that manipulations of the mineral mixture that resulted in changes in acid/base or cation/anion balance in the chick altered the incidence of abnormality. In particular, high chloride level in the diet increased the incidence of the abnormality.

Mongin and Sauveur, in "Interrelationship Between Mineral Nutrition, Acid-Based Balance, Growth and Cartilage Abnormalities," *Growth and Poultry Meat Production*, Borman, K. N. and Wilson, B. J., Eds., pp. 235–247, British Poultry Science Ltd., Edinburgh, Scotland (1977), hypothesized that the metabolic acidosis in chickens fed high dietary chloride levels caused tibial dyschondroplasia because of impaired bone mineralization resulting from alteration of vitamin D metabolism.

Figure 1:
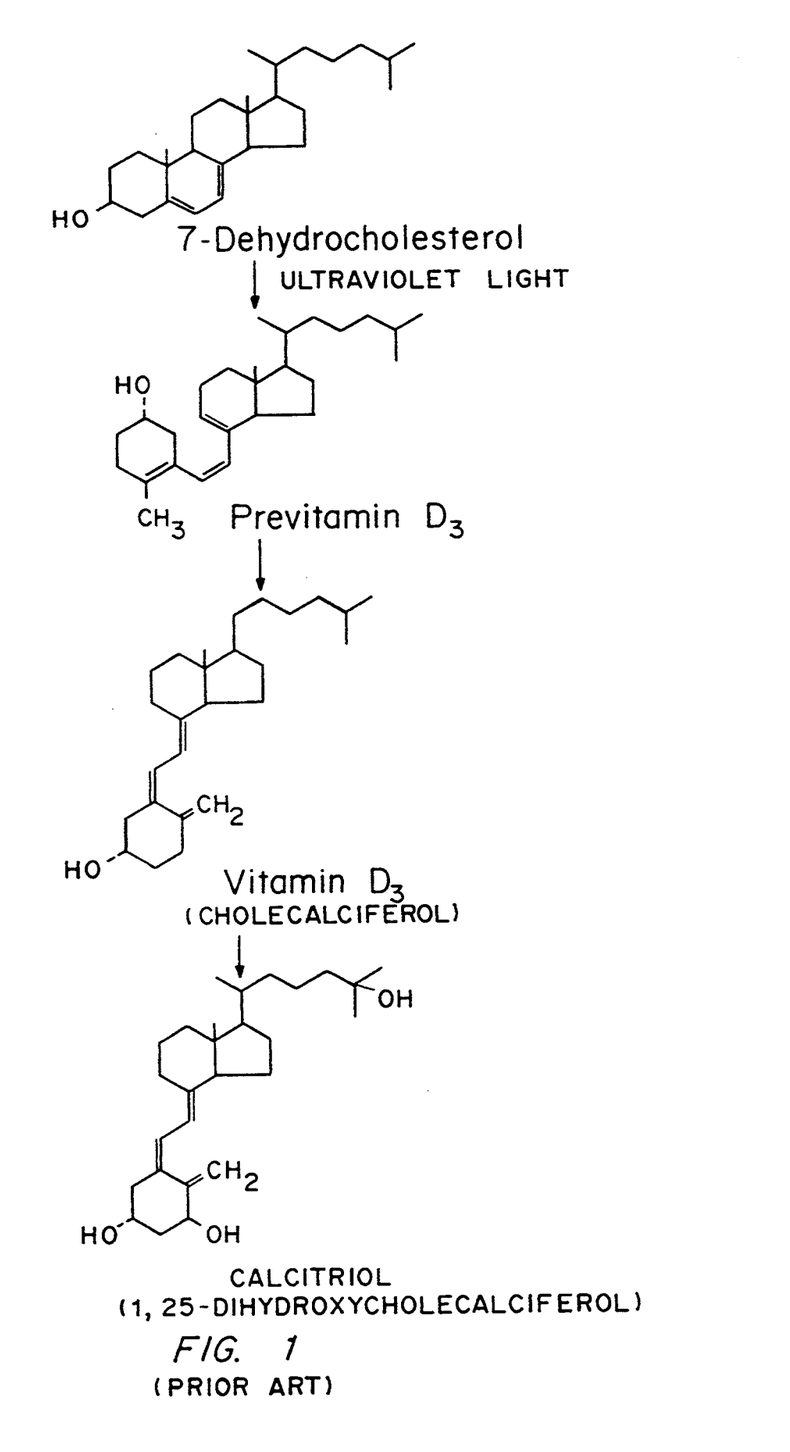
FIG. 1 is a drawing of the chemical structures of the synthesis of vitamin $D_3$ from 7-dehydrocholesterol to previtamin $D_3$ to vitamin $D_3$ and the metabolism of vitamin $D_3$ to 1,25-dihydroxycholecalciferol.
Figure 2:
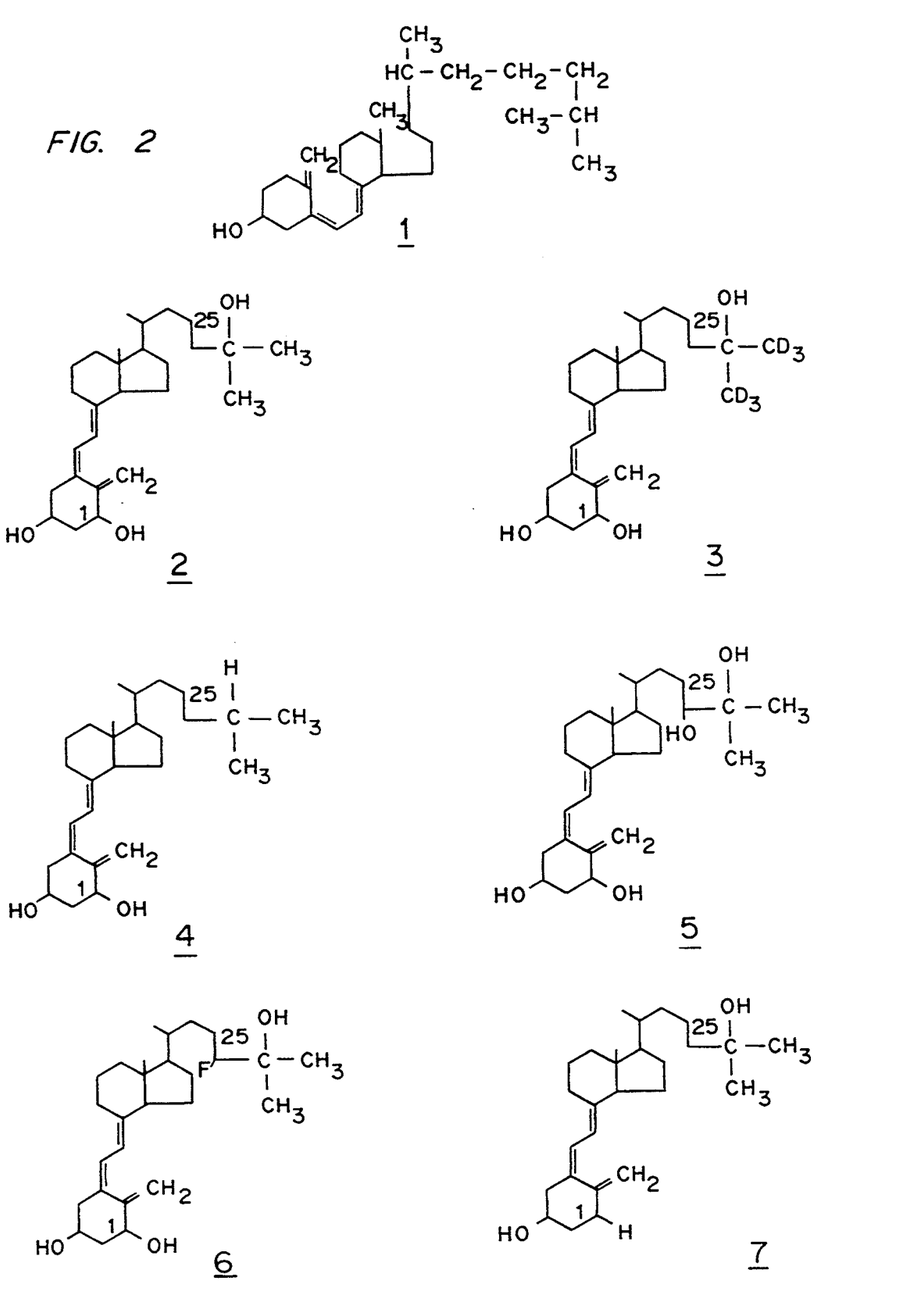
FIG. 2 is a drawing of the chemical structures of vitamin $D_3$ (cholecalciferol) (1), 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), and 25-hydroxycholecalciferol (7) as used in the methods and compositions described herein.
Figure 3:
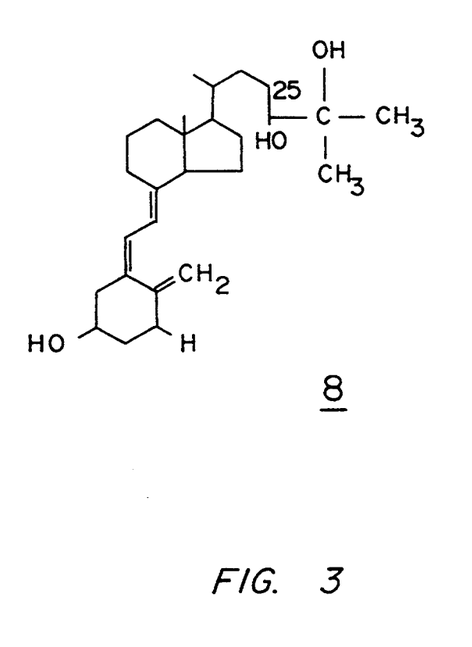
FIG. 3 is a drawing of the chemical structure of 24,25-dihydroxycholecalciferol (8).

In most animals, including humans, vitamin $D_3$ (cholecalciferol) is metabolized first by hydroxylation at the $C_{25}$ position to 25-hydroxycalciferol by one or more enzymes present in the liver, and then hydroxylation of the 25-hydroxycalciferol at the $C_1$ position to calcitriol (1,25-dihydroxycholecalciferol) by one or more enzymes present in the kidneys. A flow chart showing the chemical structures involved in vitamin D derivation and metabolism is shown in FIG. 1.

Chickens made acidotic by administration of ammonium chloride show reduced conversion of 25(OH)$D_3$ to 1,25(OH)$_2D_3$, although the production of 24,25-dihydroxycholecalciferol (24,25(OH)$_2D_3$) from 25(OH)$D_3$ is not consistently affected by acidosis as also reported by Sauveur and Mongin in "Influence of Dietary Level of Chloride, Sodium and Potassium on Chick Cartilage Abnormalities," *Proceedings of XV World Poultry Congress*, pp. 180–181 (1977).

However, supplementation of chickens with 20 ng/day of either 1,25-dihydroxycholecalciferol (1,25(OH)$_2D_3$) or 24,25-dihydroxycholecalciferol (24,25(OH)$_2D_3$) has been demonstrated to have no effect on the incidence of tibial dyschondroplasia, as described by Edwards in "Studies on the Etiology of Tibial Dyschondroplasia in Chickens", *J. Nutr.*, 114:1001 (1984).

Calcium and phosphorus levels in the diet have been found to be major nutritional factors influencing the expression of tibial dyschondroplasia. High calcium in the feed retards development of the lesion, whereas high phosphorus levels appear to accentuate the development of the lesions, as reported by Edwards and Veltmann, "The Role of Calcium and Phosphorus in the Etiology of Tibial Dyschondroplasia in Young Chicks," *J. Nutr.*, 13:1568 (1983).

Increases in the magnesium content of the chick diet decrease the incidence of tibial dyschondroplasia; however, the effect of magnesium is not as strong as that of calcium,, as demonstrated by Edwards, "Studies on the Etiology of Tibial Dyschondroplasia in Chickens" *J. Nutr.*, 114:1001 (1984).

Given the large economic loss to meat producers caused by animals afflicted with tibial dyschondroplasia as well as the discomfort of the afflicted animal and the resulting unsanitary conditions caused by the diseased dysfunctional animal, it would be of great benefit to find an effective method and compositions to reduce the incidence of this disease.

U.S. patent application Ser. No. 07/630,748, filed December 20, 1990, now U.S. Pat. No. 5,154,925 of which this is a continuation-in-part, discloses a method for treating tibial dyschondroplasia in fowl and other animals by administering to the animals a vitamin $D_3$ derivative including 1,25-dihydroxycholecalciferol; 1,25-dihydroxy-26,27-hexadeuterocholecalciferol; 1-hydroxycholecalciferol; 1,24,25-trihydroxycholecalciferol; 1,25-dihydroxy-24-fluorocholecalciferol; 25-hydroxycholecalciferol or combinations thereof. The derivative is administered or fed to animals in a pharmaceutical carrier including animal feed in a concentration between 0.10 and 20 micrograms of a vitamin $D_3$ derivative per kilogram of body weight per day. U.S. Ser. No. 07/630,748 U.S. Pat. No. 5,154,925 will issue with claims directed to administration of the vitamin $D_3$ derivatives 1,25-dihydroxy-26,27-hexadeuterocholecalciferol; 1,24,25-trihydroxycholecalciferol; and 1,25-dihydroxy-24-fluorocholecalciferol to fowl and other animals in a pharmaceutically acceptable carrier including animal feed.

It is therefore an object of the present invention to provide additional methods and compositions for the treatment and prevention of tibial dyschondroplasia in animals.

It is a further object of the present invention to provide methods and compositions for enhancing phytate phosphorus utilization in animals.

It is a further object of the present invention to provide a method and compositions for enhancing phytate phosphorus utilization while preventing or treating tibial dyschondroplasia.

It is a further object of the present invention to provide methods and compositions for decreasing phosphorus contamination of soil by animals.

It is a further object of the present invention to provide economical animal feed compositions containing reduced levels of supplemental calcium and phosphorus.

SUMMARY OF THE INVENTION

The methods described herein include feeding animals a feed composition containing an effective amount of a hydroxylated metabolite, or derivative, of vitamin $D_3$, including 1,25-dihydroxycholecalciferol; 1,25-dihydroxy-26,27-hexadeuterocholecalciferol; 1-hydroxycholecalciferol; 1,24,25-trihydroxycholecalciferol; 1,25-dihydroxy-24-fluorocholecalciferol; 25-hydroxycholecalciferol, or combinations thereof, in animal feed. Feed compositions containing an amount of vitamin $D_3$ derivative effective for enhancing phytate phosphorus utilization and treatment or prevention of tibial dyschondroplasia contain between 1 and 10 micrograms derivative per kilogram feed.

It has been discovered that feeding a feed composition containing one or more of the above-defined 1-hydroxy vitamin $D_3$ derivatives increases calcium utilization, so less dietary calcium is needed. A reduction in dietary calcium enhances phytate phosphorus utilization so that less supplemental phosphorus is required in the diet. Concurrent administration of phytase further enhances phytate phosphorus utilization.

For prevention of tibial dyschondroplasia, a feed composition containing between 1 and 10 micrograms of one or more of the above-defined hydroxylated vitamin $D_3$ derivatives per kilogram of feed is fed on the first day of life and is continued for at least three weeks. Treatment of tibial dyschondroplasia already established in poultry is achieved by feeding the feed composition as soon as the disease is discovered and continuing treatment until the animal is cured.

DETAILED DESCRIPTION OF THE INVENTION

Methods and compositions for enhanced phytate phosphorus utilization and the treatment and prevention of tibial dyschondroplasia in animals are provided herein. Enhancement of phytate phosphorus utilization results in more economical food production by reducing the need for dietary calcium and phosphorus supplementation and reducing the amount of environmentally-hazardous phosphate excreted by the animal. Treatment or prevention of tibial dyschondroplasia improves the health of the animals and the sanitary conditions of the animal facility, and allows more animals to be successfully processed before and after slaughter.

Enhancement of Phytate Phosphorus Utilization

A method for enhancement of phytate phosphorus utilization is provided that includes feeding to animals an animal feed composition containing an effective amount of a 1-hydroxy vitamin $D_3$ derivative including 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), and combinations thereof.

Because the composition increases the utilization of calcium from the diet, the diet, such as an animal feed diet, contains lower levels of calcium without risk of adverse consequences such as bone deformity or breakage. Preferably, the total concentration of calcium in the diet is between 0.5 and 1.3% by weight. Most preferably, the calcium concentration is less than 1%.

The reduced calcium levels cause enhancement of phytate phosphorus utilization allowing a reduction in the amount of supplemental phosphorus supplied in the diet and a reduction in the amount of phosphorus excreted by the animal. Preferably, the total concentration of phosphorus in the diet is between 0.4 and 0.9% by weight.

The composition can additionally include phytase to enhance phytate phosphorus utilization to an even greater extent. Phytase is an enzyme, normally isolated in large quantities from *E. coli* or *Asperigillus ficuum*, that converts phytate phosphorus to inorganic phosphate ions. Preferably, active phytase is added to the composition by spraying feed with an effective amount of a solution of active phytase after the feed has been formed into pellets to avoid inactivation of the enzyme by exposure to elevated temperatures during the pelleting process. Most preferably, the feed contains between 30 and 600 units of active phytase per kilogram feed.

Prevention or Treatment of Tibial Dyschondroplasia

A method for the treatment or prevention of tibial dyschondroplasia is provided that includes feeding animals an animal feed composition containing an effective amount of a 1-hydroxy vitamin $D_3$ derivative including 1,25-dihydroxycholecalciferol (2), 1,25-dihydroxy-26,27hexadeuterocholecalciferol (3), 1-hydroxycholecalciferol (4), 1,24,25trihydroxycholecalciferol (5), 1,25-dihydroxy-24-fluorocholecalciferol (6), 25-hydroxycholecalciferol (7), and combinations thereof.

Preparation of Vitamin D Derivatives

The vitamin $D_3$ derivatives described herein can be prepared by the following procedures, the teachings of which are incorporated by reference herein.

1,25-Dihydroxycholecalciferol can be prepared as described in *Biochemistry* 10(14), 2799 (1971), and U.S. Pat. No. 4,310,467 and 3,697,559.

1,25-Dihydroxy-26,27-hexadeuterocholecalciferol can be prepared as described for the synthesis of 1,25-dihydroxycholecalciferol in *Tet. Let.* 40, 4147 (1972), with the substitution of a trideuteromethyl Grignard reagent in place of the methyl Grignard reagent used to add the carbons at the 26 and 27 positions.

1-Hydroxycholecalciferol can be prepared by the methods described in *J. Am. Chem. Soc.* 95(8), 2748 (1973) and U.S. Pat. No. 3,741,996.

1,24,25-Trihydroxycholecalciferol can be prepared by the method described in U.S. Pat. No. 3,847,955.

1,25-Dihydroxy-24-fluorocholecalciferol can be prepared by the procedure described in J. Org. Chem., 53(5), 1040 (1988).

25-Hydroxycholecalciferol can be prepared as described in U.S. Pat. Nos. 4,310,467 and 3,565,924.

Animals to Which the Composition is Administered

The methods and compositions described herein are particularly useful for enhancing phytate phosphorus utilization and reducing the incidence of tibial dyschondroplasia in chickens, especially broiler chickens and egg-laying chickens.

The methods and compositions are equally effective in enhancing phytate phosphorus utilization in other types of monogastric animals, including but not limited to, humans, swine, and other fowl including turkeys, pheasants, and ducks. The animals to which the animal feed containing the vitamin $D_3$ derivative is fed are generally not vitamin D-deficient, receiving an adequate supply of vitamin D in the diet and exposure to adequate amounts of sunlight.

Feeding the above-described feed compositions according to the methods described herein are also effective in preventing or treating tibial dyschondroplasia by reducing or reversing the development of abnormal cartilage at the proximal end of the tibia in a variety of animals including, but not limited to, swine dogs, rabbits, cattle, fish and other fowl including turkeys, pheasants and ducks. For example, Great Danes have a particular problem with tibial dyschondroplasia due to their rapid growth.

Effective Dosage Range and Method of Administration

An effective dosage of one or more of the vitamin $D_3$ derivatives described herein for either enhancement of phytate phosphorus utilization or prevention or treatment of tibial dyschondroplasia is between 0.1 and 20 micrograms per kilogram of body weight per day. However, it is inconvenient to weigh the animal and adjust and administer the dosage each day. It is more convenient and economical to prepare an animal feed or water composition containing a fixed amount of vitamin $D_3$ derivative. As the animal becomes larger, it will consume greater quantities of feed or water containing the vitamin $D_3$ derivative, thereby self-regulating administration of an appropriate dosage of the derivative.

For the foregoing reasons, the vitamin $D_3$ derivative is preferably fed to animals in an animal feed composition containing between 1 and 10 micrograms derivative per kilogram feed. A more preferred animal feed composition contains between 3 and 6 micrograms derivative per kilogram feed. Most preferably, the animal feed composition is fed in feed containing approximately 5 micrograms vitamin $D_3$ derivative per kilogram feed. Dosages above 10 micrograms derivative per kilogram feed tend to cause a decreased animal growth rate.

It will be understood by those skilled in the art that the vitamin $D_3$ derivative could also be administered as a water composition wherein the concentration of derivative in the water is approximately one-half the concentration of derivative described above for use in feed because animals normally consume two volumes of water for every one volume of dry food. Therefore, the concentration of vitamin $D_3$ derivative in water is preferably between 0.5 and 5 micrograms per kilogram water.

Enhancement of both phytate phosphorus utilization and prevention of tibial dyschondroplasia can be achieved by feeding one or more of the vitamin D derivatives in accordance with the methods described herein in animal feed from birth throughout the life of the animal. For example, in poultry, treatment is preferably begun at one day of age, and continued for at least three to four weeks to prevent the onset of tibial dyschondroplasia. Feeding the vitamin $D_3$ derivatives described herein to animals older than one day of age will continue to provide the desired therapeutic effect, but will be slightly less effective at preventing the onset of the tibial dyschondroplasia.

The compositions can also be fed in a feed composition as a treatment for tibial dyschondroplasia already established in the animal. The same dosages are used as for prevention of the disease. The compositions should be fed to the animal as soon as the disease is discovered, and continued until the animal is cured. However, feeding the feed compositions at this time will not reverse the abnormal shape of bones caused by the disease.

The effectiveness of feeding the composition on enhancement of phytate phosphorus utilization in poultry and other animals can be determined by measuring the phosphorus content of the feed, the phosphorus content of feces collected from the animals, and calculating the amount of phosphorus retained as described in the examples below.

The effectiveness of feeding the compositions on prevention or treatment of tibial dyschondroplasia in fowl can be determined by making a longitudinal cut across the tibia and inspecting it for incidence and severity of the disease, as described below in the examples.

The effectiveness of feeding the compositions containing the vitamin $D_3$ derivatives on prevention or treatment of dyschondroplasia in other animals can be determined by internal inspection of the bone for abnormal cartilage development or external inspection of bone for irregularities, bowed shape, or weakness.

Poultry Feed Composition for Phytate Phosphorus Enhancement

A preferred poultry feed composition for enhancement of phytate phosphorus utilization in poultry contains an effective amount of a 1-hydroxylated vitamin $D_3$ derivative such as 1,25-dihydroxycholecalciferol (2), 1,25-dihydroxy-26,27-hexadeuterocholecalciferol (3), 1-hydroxycholecalciferol 1,24,25trihydroxycholecalciferol (5), 1,25-dihydroxy-24-fluorocholecalciferol (6), or a combination thereof, in combination with sources of energy such as corn, fat and soybean meal; sources of protein such as corn and soybean meal; mineral sources such as iodized sodium chloride; amino acids such as D,L-methionine; a vitamin mixture; a trace mineral mixture; selenium concentrate (0.02% sodium selenite); and a calcium source such as limestone.

The vitamin mixture in the poultry or fowl feed composition provides in milligrams/kilogram of diet (except as noted) vitamin A (as all-trans-retinyl acetate), 5,500 IU; vitamin $D_3$ (cholecalciferol), 1100 ICU or 27.5 micrograms; vitamin E (all-rac-alpha-tocopheryl acetate), 11 IU; riboflavin, 4.4; calcium pantothenate, 12; nicotinic acid, 44; choline chloride, 220; vitamin $B_{12}$, 9 micrograms; vitamin $B_6$, 3.0; menadione (as menadione sodium bisulfite), 1.1; thiamin (as thiamin mononitrate) 2.2; folic acid, 3; biotin, 0.3; and ethoxyquin, 125.

The trace mineral mixture provides in milligrams per kilogram of diet $MnO_2$, 222; ZnO, 150, $FeSO_4\text{-}7H_2O$, 200; $FeCO_3$, 83; $C_uSO_4$, 29; and $Ca(IO_3)_2$, 15.

The vitamin $D_3$ derivative is preferably combined with the feed by first dissolving it in an alcohol, adding the solution to feed, and mixing the feed to evenly distribute the dissolved derivative.

A phytase solution is preferably added to the feed by first diluting the phytase with a powder, such as powdered soybean meal flour and then mixing the diluted phytase with the feed composition containing the vitamin D derivative. Alternatively, the phytase solution can be sprayed onto the feed and allowed o dry. Preferably, the feed contains between 30 and 600 units of active phytase per kilogram feed. Active phytase is available commercially from the Sigma Chemical Company, St. Louis, Mo.

The ingredients of a supplemented chicken feed to which the vitamin $D_3$ derivatives described herein may be added in the above-described dosages for enhanced phytate utilization in chickens are described in Table 1. The amounts indicated are given in percent by weight. It will be understood by those skilled in the art that the active vitamin $D_3$ derivatives described herein can also be fed in combination with other commercially formulated or similar feeds for chickens and other animals.

TABLE 1

| Chicken Feed Composition for Phytate Phosphorus Enhancement | |
|---|---|
| Ingredients | Amounts |
| Ground yellow corn | 57.63 |
| Soybean meal (dehulled) | 35.00 |
| Poultry fat (stabilized) | 5.00 |
| Iodized sodium chloride | 0.45 |
| D,L-Methionine (98%) | 0.20 |
| Vitamin premix (as described above) | 0.25 |
| Trace mineral premix (as described above) | 0.10 |
| Se concentrate (0.02% from sodium selenite) | 0.05 |
| Limestone | 1.32 |

The vitamin $D_3$ derivatives described herein are efficacious for the enhancement of phytate phosphorus utilization when added to the above-described feed which has a calcium concentration of 0.5%. Broiler chickens are typically fed a diet which has a range of calcium of 0.7 to 1.4% by weight, while egg laying hens are fed a diet with a higher calcium level. This reduced level of calcium is achieved because the animal feed contains no dicalcium phosphate. Any calcium present in the feed is due to the presence of limestone.

A reduced level of phosphorus of 0.3% is also achieved by feeding the above-described animal feed lacking dicalcium phosphate. The phosphate present is due to phytate phosphorus alone.

Poultry Feed Composition for Tibial Dyschondroplasia

A preferred poultry feed composition for treatment or prevention of tibial dyschondroplasia in poultry contains an effective amount of a hydroxylated vitamin $D_3$ derivative such as 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), 25-hydroxycalciferol (7), or a combination thereof, in combination with sources of energy such as corn, fat and soybean meal; sources of protein such as corn and soybean meal; mineral sources such as iodized sodium chloride; amino acids such as D,L-methionine; a vitamin mixture; a trace mineral mixture; selenium concentrate (0.02% sodium selenite); a phosphorus source such as dicalcium phosphate; and calcium sources such as dicalcium phosphate and limestone.

The vitamin and trace mineral mixtures for the chicken feed composition for the treatment or prevention of tibial dyschondroplasia are the same as those set forth above for the chicken feed composition for enhancement of phytate phosphorus utilization.

The ingredients of a supplemented chicken feed to which the vitamin $D_3$ derivatives described herein may be added in the above-described dosages for treatment or prevention of tibial dyschondroplasia in chickens are described in Table 2. The amounts indicated are given in percent by weight. It will be understood by those skilled in the art that the active vitamin $D_3$ derivatives described herein can also be fed in combination with other commercially formulated or similar feeds for chickens and other animals.

TABLE 2

| Chicken Feed Composition for Tibial Dyschondroplasia | |
|---|---|
| Ingredients | Amounts |
| Ground yellow corn | 56.81 |
| Soybean meal (dehulled) | 35.00 |
| Poultry fat (stabilized) | 5.00 |
| Iodized sodium chloride | 0.45 |
| D,L-Methionine (98%) | 0.20 |
| Vitamin premix (as described above) | 0.25 |
| Trace mineral premix (as described above) | 0.10 |
| Se concentrate (0.02% from sodium selenite) | 0.05 |
| Dicalcium phosphate (feed grade) | 1.86 |
| Limestone | 0.28 |

Chickens fed the diet described in Table 2 without the vitamin $D_3$ derivatives described herein will have a higher than normal incidence of tibial dyschondroplasia even though the diet contains a high level of vitamin $D_3$ because the diet has a high level of chloride and phosphorus and a low level of calcium. The average analyzed values for the chicken feed described in Table 2 are 0.32% chloride, 0.76% phosphorus, and 0.75% calcium.

The vitamin $D_3$ derivatives described herein are efficacious for the treatment or prevention of tibial dyschondroplasia in a feed having any calcium concentration, particularly those with a calcium composition of less than 2.5% by weight. However, a feed composition useful for both enhancement of phytate phosphorus utilization and prevention or treatment of tibial dyschondroplasia preferably has a calcium concentration of between 0.5 and 1.3% as described above.

A control system to test the effectiveness of the vitamin $D_3$ derivatives on reducing the incidence of tibial dyschondroplasia in fowl was developed using disulfiram [bis(diethylthiocarbamyl)disulfide], an alcohol deterrent, in a dietary dosage of approximately 30 mg/kg feed per day. Disulfiram supplementation lowers the absorption of calcium when given as an oral dose compared to controls. It is known that thiruram [bis(dimethylthiocarbamyl)disulfide], a compound used as a fungicide and bactericide which is structurally close to disulfiram and which also causes tibial dyschondroplasia, creates a rapid loss of intramuscularly-injected calcium immediately after dosing. This suggests that calcium in the blood and soft tissues (gastrointestinal tract) can be lost more easily from the birds receiving thiruram or disulfiram but that once the calcium goes into the bone both thiruram and disulfiram have little effect on turnover.

The present methods and compositions will be further understood with reference to the following non-limiting examples.

Example 1

Enhancement of Phytase Utilization with Vitamin $D_3$ Derivatives

The effectiveness of 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), and 1,25-dihydroxy-24-fluorocholecalciferol (6) in enhancing phytate phosphorus utilization in chickens has been demonstrated using the following experimental procedures.

Newly hatched Petersen X Arbor Acre cockerels obtained from a commercial hatchery were used. Animals were housed in electrically heated Petersime battery brooders with wire-mesh floors located in a room in which the temperature was maintained at 22° C., fluorescent lights were on 24 hours each day in the room and the cages, and sunlight was present during the day from large windows. No attempt was made to limit the natural production of vitamin $D_3$. Feed and water were available to the chickens at all times.

Ten newly hatched birds were randomly placed in each section of the Petersime batteries until the birds were nine days old. The measurements described below were calculated on a pen basis; all statistical analyses were conducted on pen averages. Blood samples were taken by cardiac puncture with heparinized syringes from one randomly chosen bird from each pen on the ninth day before weighing the birds. The blood samples were analyzed for plasma total calcium using Technicon Auto Analyzer Methodology set forth in a 1969 publication by the Technicon Instrument Co. Ltd. (Basingstoke, Hants, U.K.) and dialyzable phosphorus using Technicon Auto Analyzer Methodology set forth in a 1970 publication by the Technicon Instrument Co. Ltd.

The basal diet used in these studies is shown in Table 1 above. The basal diet contained 1100 ICU/kg (27.5 microgram/kg) of added $D_3$ and is low in calcium and phosphorus, having average analyzed values of 0.5% calcium and 0.3% phosphorus.

At nine days of age, pen body weights were obtained for all birds and their feed consumption was recorded. All birds were then killed by asphyxiation and examined at random for tibial dyschondroplasia and rickets by making a longitudinal cut across the tibia and scoring for incidence and severity of tibial dyschondroplasia in accordance with the method described in H. Edwards and J. Veltmann, "The Role of Calcium and Phosphorus in the Etiology of Tibial Dyschondroplasia in Young Chicks", *J. Nutr.*, 113, 1568 (1983), which is incorporated herein by reference. Briefly, using a three week old chicken as the reference animal, a score of zero indicates normal cartilage which is narrow with little irregularities. A score of one indicates cartilage which is thickened or shows considerable irregularities. A score of two indicates that the cartilage is thickened and there is evidence of persisting prehypertrophic cartilage that is not calcified and which has not been invaded by vessels from the metaphysis. Deep irregularities are apparent. A score of three indicates a large mass of cartilage in the proximal end of the tibia. The birds were also scored for phosphorus deficient rickets at the same time they were scored for tibial dyschondroplasia. Chickens which had normal proliferating prehypertrophied zone and a lengthened metaphyseal primary spongiosa were classified as phosphorus deficient rickets. The left tibia was removed for bone ash determination on the fat-free bone.

In each experiment, the droppings from all of the chickens for the entire nine day experimental period were collected at the end of the experiment. They were dried in a force draft oven at 70° C., weighed, and ground in a Wiley Mill. Samples were then taken and, with a feed sample, analyzed for calcium by the fluorometric method of Hill, *Clin. Chem.* 2:122–130 (1955), phosphorus by the method of O'Neill and Webb, *J. Sci Food Agric.* 21:217–219 (1970), and phytate, or phytin, phosphorus by the method of Common, *J. Agric. Sci.* 30:113–131 (1940), the methods of which are incorporated by reference herein.

Phytate phosphorus in feed and feces samples was also determined by a modification of the method reported by Sandberg and Ahderinne, *J. Food Sci.* 51:547–550 (1986), the methods of which are incorporated by reference herein, for determination of phytate in feed and feed ingredients. The method has been modified and tested to allow high pressure liquid chromatography determination of phytate in poultry feces as follows. Pulverized dried excreta of 0.2 g (0.5 g for feed sample) was extracted using 20 ml 0.5M HCl under vigorous mechanical agitation at room temperature for two hours. The extract was filtered through glass microfiber filter paper #934-AH (Whatman International, Maidstone, England) under vacuum. Four milliliters of the filtrate was then diluted with 16 ml of deionized water. The inositol phosphates were separated from the diluted filtrate solution and were concentrated using anion-exchange column chromatography. A glass column of 0.7×15 cm with a glass filter at the distal end was packed with 2 ml of anion-exchange resin (AG 1-x8, 200–400 mesh) (Bio-Rad, Richmond, Calif.) developed overnight in 0.025M HCl.

The diluted filtrate solution of 20 ml was passed through the anion-exchange column at a flow rate of approximately 0.4 ml/min, the column was then washed with 4 ml 0.025M HCl. Inositol phosphates were removed from the chromatographic column using 20 ml 2M HCl. The eluate was collected in a 20 ml scintillation vial. An 8 ml fraction of eluent was freeze-dried.

The dried sample was then reconstituted with 0.8 ml of a filtered mobile phase consisting of 0.05M formic acid:methanol (HPLC grade) 50:50, 1.5 ml/100 ml of tetrabutylammonium hydroxide (TBA-OH, 40% in water) (Sigma, St. Louis, Mo.) and 5 mM of ethylenediaminetetraacetic acid (EDTA). The pH of the mobile phase was adjusted to 4.3 by the addition of 6M sulfuric acid. The mobile phase was filtered through a nylon membrane filter (0.45 micron pore size) under vacuum.

The analysis was performed using an HPLC pump, Eldex Model AA-72-S (Eldex, San Carlos, Calif.) equipped with a reverse phase C-18 Waters Radialpak column (Waters, Milford, Mass.) having a 5 mm inside diameter and 5 micron particle size. The inositol phosphates were detected by refractive index using a Waters Differential Refractometer, Model R401 (Waters, Milford, Mass.). The optimal flow rate was 1.5 ml/min. Retention times and peak areas were measured by a Hewlett Packard Model 3390A integrator (Hewlett Packard, Palo Alto, Calif.). Samples were injected into a 20 microliter Rheodyne Model 7125 loop (Rheodyne, Cotati, Calif.). Sodium phytate was used as both the internal and external standard. The linearity of phytate concentration versus peak area was investigated by 20 microliter injections of solutions containing 5.6, 11.2, 16.8, and 22.4 micrograms of phytate.

In the first experiment, a sample containing a known amount of added hexaphosphoinositol was run with each sample to determine recovery. For the 24 fecal samples in this experiment, the recovery averaged 101.5%. Recovery studies were not conducted in later experiments and recovery was assumed to be 100%.

Experiment 1

Each of the twelve different dietary treatments described below were provided to two pens containing ten birds per pen.
1. One diet was a basal diet lacking supplemented inorganic phosphorus, phytase or the vitamin $D_3$ derivative 1,25-$(OH)_2D_3(2)$.
2. Three diets contained graded levels of phosphorus (0.1, 0.2 and 0.3%) from reagent grade $Na_2HPO_4H_2O$ which is indicated by the symbol P in the tables.
3. Four diets contained graded levels of phytase (Sigma Chemical Co., St. Louis, Mo.), at 75, 150, 300 and 600 units/kg of feed. The phytase was first mixed with powdered soybean meal flour, and the phytase and flour mixture was combined with the feed.
4. Four diets contained the four levels of phytase described above plus 10 micrograms/kg of 1,25-$(OH)_2D_3$. The derivative was first diluted with propylene glycol to a concentration of 10 micrograms per milliliter, and then the solution was mixed with feed in a Hobart mixer for 10 minutes.

All chickens were fed a corn-soybean diet containing only 0.67% calcium, 0.34% phosphorus, and a vitamin mixture supplying 1100 ICU $D_3$/kg of diet.

The results are shown in Tables 3A, 3B and 3C below.

Analysis of Experiment 1 Results

The birds fed the basal phosphorus-deficient diet had very low nine day weights and gain to feed ratios and developed very severe phosphorus deficient rickets. The bone ash value of 22.9% ash indicates extremely poor bone calcification. Fifty percent of the dietary phytate appeared in the feces as hexa, hepta and tetra phosphoinositol, (IP6, IP5 and IP4) indicating that only half of the phytate phosphorus in the basal diet was available to the chickens.

The addition of phosphorus to the diet resulted in increased nine day weights, gain:feed ratios, blood plasma phosphorus and bone ash. The incidence of phosphorus-deficient rickets was decreased. The amount of phosphorus in the feces was approximately the same.

The addition of phytase to the diet resulted in an increase in nine day weight and a small decrease in the amount of hexaphosphoinositol in the feces. There was no significant increase in bone ash. The calculated phytate retention value was 60.7% for birds fed the highest level of phytase.

The animals given feed containing 1,25-(OH)$_2$D$_3$(2) and phytase had higher nine day body weights than those fed the basal diet. The addition of 1,25-(OH)$_2$D$_3$(2) and phytase to the diet resulted in increased bone ash values and a significant decrease in the levels of hexa and penta phosphoinositol in the feces as compared to all other treatments. The level of tetraphosphoinositol was so low in feces that it was not detectable with the method used. The calculated retention data indicate that these animals utilized from 76 to 88% of the phytate phosphorus consumed as compared to 50% by the animals fed the basal diet and 52 to 60% by the animals fed the basal diet plus phytase alone.

The addition of 1,25-(OH)2D$_3$ caused a large increase in the utilization of phytate phosphorus as indicated from the bone ash values and amounts of phytate excreted in the feces.

TABLE 3A

Effect of dietary phosphorus levels and phytase and/or 1,25-(OH)$_2$D$_3$ supplementation on growth, development of tibial dyschondroplasia and Ca, P, and phytate phosphorus retention by broilers

| Treatments | Wt. 9-d g | Gain: feed | Bone ash % | Tibial dyschondroplasia Incidence % | Score | #3 Scores % | Phosphorus rickets incidence % | Retention by the broiler Calcium % | Phosphorus % | Phytate phosphorus[1] % |
|---|---|---|---|---|---|---|---|---|---|---|
| Basal 0% P | 133 | .672 | 22.9 | 12 | 2.00 | 7 | 41 | 49.53 | 46.47 | 50.50 |
| .1% P | 168 | .753 | 21.8 | 35 | 1.80 | 10 | 5 | 52.76 | 40.72 | 46.51 |
| .2% P | 164 | .701 | 36.5 | 15 | .67 | 0 | 0 | 60.87 | 28.56 | 67.78 |
| .3% P | 163 | .701 | 38.5 | 5 | .50 | 0 | 0 | 62.20 | 9.50 | 50.72 |
| 75 units Phytase | 144 | .724 | 23.9 | 0 | 0 | 0 | 33 | 47.06 | 47.2 | 56.36 |
| 150 units Phytase | 148 | .716 | 24.7 | 5 | .50 | 0 | 28 | 44.80 | 53.55 | 59.06 |
| 300 units Phytase | 142 | .707 | 24.4 | 0 | 0 | 0 | 40 | 42.62 | 49.04 | 52.67 |
| 600 units Phytase | 153 | .733 | 26.5 | 25 | 1.63 | 10 | 30 | 43.54 | 55.39 | 64.85 |
| 75 units P + 10 μg/kg 1,25-(OH)$_2$D$_3$ | 162 | .727 | 31.7 | 0 | 0 | 0 | 5 | 51.14 | 61.73 | 80.60 |
| 150 units P + 10 μg/kg 1,25-(OH)$_2$D$_3$ | 152 | .700 | 32.1 | 5 | .50 | 0 | 0 | 51.15 | 67.24 | 87.41 |
| 300 units P + 10 μg/kg 1,25-(OH)$_2$D$_3$ | 153 | .690 | 33.5 | 5 | .50 | 0 | 5 | 56.80 | 65.50 | 83.36 |
| 600 units P + 10 μg/kg 1,25-(OH)$_2$D$_3$ | 160 | .729 | 34.0 | 5 | .50 | 0 | 0 | 53.50 | 67.31 | 82.23 |
| Mean ± SEM | 153 ± 5 | .713 ± .016 | 30.0 ± .9 | 9 ± 8 | .72 ± .51 | 2 ± 3 | 15 ± 8 | 51.33 ± 3.29 | 49.35 ± 1.60 | 65.17 ± 3.99 |

[1]Total feed and fecal phytate phosphorus determined by the ferric chloride method.

TABLE 3B

Effect of dietary phosphorus levels and phytase and/or 1,25-(OH)$_2$D$_3$ supplementation on blood Ca and P, phytin phosphorus excretion, and calculated retention of phytate phosphorus

| Treatments | Blood plasma Calcium mg/kg | Dialyzable phosphorus mg/kg | Phytin phosphorus excretion expressed as a percent of total phytin phosphorus ingested IP4 % | IP5 % | IP6 % | Total excreted % | Phytin Phosphorus retained (100 - total excreted) % |
|---|---|---|---|---|---|---|---|
| Basal 0% P | 136 | 20.0 | .25 | 5.20 | 44.83 | 50.4 | 49.8 |
| .1% P | 142 | 20.5 | .71 | 5.76 | 46.92 | 53.4 | 46.7 |
| .2% P | 112 | 59.5 | .81 | 2.70 | 37.06 | 40.6 | 59.5 |
| .3% P | 105 | 75.0 | 1.46 | 6.87 | 46.00 | 54.4 | 45.9 |
| 75 units Phytase | 137 | 15.8 | .28 | 5.05 | 43.12 | 48.4 | 51.6 |
| 150 units Phytase | 145 | 14.8 | .00 | 4.23 | 37.46 | 41.7 | 58.5 |
| 300 units Phytase | 161 | 7.67 | .39 | 5.14 | 40.66 | 46.2 | 53.8 |
| 600 units Phytase | 145 | 1.83 | .43 | 4.48 | 34.46 | 39.4 | 60.7 |
| 75 units P + 10 μg/kg 1,25-(OH)$_2$D$_3$ | 168 | 18.0 | .00 | 1.28 | 22.43 | 23.8 | 76.3 |
| 150 units P + 10 μg/kg 1,25-(OH)$_2$D$_3$ | 178 | 14.0 | .00 | 1.12 | 19.53 | 20.7 | 79.4 |
| 300 units P + 10 μg/kg 1,25-(OH)$_2$D$_3$ | 157 | 24.0 | .000 | .61 | 12.91 | 13.5 | 86.5 |
| 600 units P + 10 μg/kg 1,25-(OH)$_2$D$_3$ | 148 | 25.0 | .000 | .13 | 12.07 | 12.3 | 87.8 |
| Mean ± SEM | 144 ± 14 | 24.7 ± 6.6 | .36 ± .05 | 3.55 ± .75 | 33.12 ± 2.54 | 37.0 ± 3.1 | 63.0 ± 3.1 |

TABLE 3C

Phytate content of fecal samples, determined by the ferric chloride and HPLC procedures and calculated retention of phytate phosphorus by each procedure

| Treatments | Food[1] consumed g | Feces excreted g | Phytate Phosphorus in feces by FeCl[3] mg/g | Phytate phosphorus in feces by HPLC procedure | | | | Phytate phosphorus retention | |
|---|---|---|---|---|---|---|---|---|---|
| | | | | IP4 mg/g | IP5 mg/g | IP6 mg/g | Total mg/g | FeCl[3] | HPLC |
| Basal 0% P | 1345 | 402 | 3.53 | .025 | .490 | 4.23 | 4.75 | 51 | 50 |
| .1% P | 1660 | 451 | 3.50 | .060 | .490 | 3.99 | 4.54 | 47 | 47 |
| .2% P | 1725 | 602 | 1.97 | .065 | .230 | 3.03 | 3.32 | 68 | 60 |
| .3% P | 1715 | 606 | 2.98 | .115 | .550 | 3.68 | 4.35 | 51 | 46 |
| 75 units Phytase | 1395 | 460 | 2.87 | .025 | .435 | 3.73 | 4.19 | 56 | 52 |
| 150 units Phytase | 1305 | 434 | 2.63 | .000 | .360 | 3.18 | 3.54 | 59 | 59 |
| 300 units Phytase | 1385 | 483 | 2.93 | .030 | .410 | 3.23 | 3.68 | 53 | 54 |
| 600 units Phytase | 1500 | 491 | 2.30 | .035 | .385 | 2.96 | 3.38 | 65 | 61 |
| 75 units P + 10 μg/kg 1,25-(OH)$_2$D$_3$ | 475 | 519 | 1.17 | .000 | .105 | 1.80 | 1.90 | 81 | 76 |
| 150 units P + 10 μg/kg 1,25-(OH)$_2$D$_3$ | 1565 | 564 | 0.76 | .000 | .090 | 1.53 | 1.62 | 87 | 79 |
| 300 units P + 10 μg/kg 1,25-(OH)$_2$D$_3$ | 1510 | 522 | 1.03 | .000 | .050 | 1.06 | 1.11 | 83 | 87 |
| 600 units P + 10 μg/kg 1,25-(OH)$_2$D$_3$ | 1610 | 561 | 1.09 | .000 | .010 | 0.98 | 0.99 | 82 | 88 |
| Mean ± SEM | 1515 ± 96 | 508 ± 50 | 2.23 ± .28 | .030 ± .015 | .300 ± .067 | 2.78 ± .27 | 3.11 ± .33 | | |

Experiment 2

Each of the eight different dietary treatments set forth below were provided to three pens containing ten birds per pen.

1. One diet was a basal diet lacking supplemental inorganic phosphorus, phytase or the vitamin D derivative 1,25-(OH)$_2$D$_3$(2).
2. One diet contained 0.2% supplemental phosphorus (Na$_2$HPO$_4$H$_2$O) alone.
3. One diet contained 75 units of phytase alone.
4. One diet contained 5 micrograms/kg 1,25-(OH)$_2$D$_3$ alone.
5. One diet contained both 0.2% supplemental phosphorus plus 75 units of phytase.
6. One diet contained both 0.2% supplemental phosphorus plus 5 micrograms/kg 1,25-(OH)$_2$D$_3$.
7. One diet contained both 75 units of phytase plus 5 micrograms/kg 1,25-(OH)$_2$D$_3$.
8. One diet contained 0.2% supplemental phosphorus plus 75 units of phytase plus 5 micrograms/kg 1,25-(OH)$_2$D$_3$.

All chickens were fed a corn-soybean diet containing only 0.6% calcium, 0.34% phosphorus, and a vitamin mixture supplying 1100 ICU D$_3$/kg of diet.

The results are shown in Table 4 below.

Analysis of Experiment 2 Results

The addition of 1,25-(OH)$_2$D$_3$(2) to the diet caused an increase in the utilization of phytate phosphorus by the broiler chickens from 31% to 68%. The combination of phytase and 1,25-(OH)$_2$D$_3$ raised the utilization to 79%.

TABLE 4

Effect of 1,25-(OH)$_2$D$_3$ plus phytase

| Treatments | Wt. 9-d g | Gain: feed | Bone ash % | Tibial dyschondroplasia | | #3 scores % | Phos. rickets incidence |
|---|---|---|---|---|---|---|---|
| | | | | Incidence % | Score | | |
| Basal 0% P | 145 | .732 | 24.2 | 7 | 0.67 | 0 | 55 |
| .2% P | 170 | .721 | 34.8 | 10 | 1.00 | 3 | 0 |
| 75 units phytase | 154 | .748 | 23.7 | 7 | 0.67 | 0 | 60 |
| 5 μg/kg 1,25-(OH)$_2$D$_3$ | 172 | .760 | 29.8 | 17 | 1.00 | 0 | 10 |
| .2% P + 75 units phytase | 181 | .772 | 35.4 | 7 | 1.33 | 3 | 0 |
| .2% P + 5 μg/kg 1,25-(OH)$_2$D$_3$ | 186 | .776 | 35.9 | 3 | 1.00 | 3 | 0 |
| 75 units Phytase + 5 μg/kg 1,25-(OH)$_2$D$_3$ | 167 | .735 | 30.1 | 17 | 1.33 | 3 | 27 |
| .2% P + 75 units phytase + 5 μg/kg 1,25-(OH)$_2$D$_3$ | 178 | .772 | 35.8 | 10 | 1.67 | 3 | 7 |
| Mean ± SEM | 169 ± 4 | .752 ± .016 | 31.2 ± .6 | 10 ± .06 | 1.08 ± .60 | 2.08 ± 2.64 | 20 ± 6 |

Retention by       Metabo-

TABLE 4-continued

| | Effect of 1,25-(OH)$_2$D$_3$ plus phytase | | | | | |
|---|---|---|---|---|---|---|
| | Blood plasma | | the broiler | | | lizable |
| Treatments | Ca mg/kg | Dialyzable P mg/kg | Ca % | P % | Phytate P % | energy of diet kcal/kg |
| Basal 0% P | 133.5 | 12.2 | 29.8 | 43.6 | 31.3 | 2.88 |
| .2% P | 112.1 | 50.3 | 51.5 | 49.5 | 42.3 | 2.79 |
| 75 units phytase | 126.0 | 11.9 | 30.6 | 44.1 | 41.6 | 2.98 |
| 5 μg/kg 1,25-(OH)$_2$D$_3$ | 136.5 | 14.5 | 44.8 | 64.8 | 68.4 | 2.99 |
| .2% P + 75 units phytase | 118.3 | 61.3 | 49.3 | 51.6 | 44.4 | 2.82 |
| .2% P + 5 μg/kg 1,25-(OH)$_2$D$_3$ | 116.2 | 61.7 | 57.3 | 52.8 | 62.5 | 2.85 |
| 75 units Phytase + 5 μg/kg 1,25-(OH)$_2$D$_3$ | 119.6 | 39.7 | 46.2 | 59.5 | 79.4 | 2.84 |
| .2% P + 75 units phytase + 5 μg/kg 1,25-(OH)$_2$D$_3$ | 128.5 | 66.2 | 53.0 | 53.7 | 67.7 | 2.87 |
| Mean ± SEM | 123.8 ± 6.1 | 39.7 ± 8.7 | 45.3 ± 3.4 | 52.1 ± 2.4 | 54.7 ± 4.5 | 2.88 ± .03 |

Experiment 3

Each of the twelve different dietary treatments described below were provided to two pens containing ten birds per pen.
1. One diet was a basal diet lacking supplemental phytase or 1,25-(OH)$_2$D$_3$ (2).
2. Five diets contained graded levels of phytase from 37.5 units to 600 units.
3. One diet contained basal phytase plus 5 microgram/kg feed of 1,25-(OH)$_2$D$_3$.
4. Five diets contained graded levels of phytase plus 5 microgram/kg feed of 1,25-(OH)$_2$D$_3$.

The results are shown in Table 5 below. In Table 5, and subsequent tables, the abbreviations TDI and TDS represent tibial dyschondroplasia incidence and tibial dyschondroplasia score, respectively. N3 indicates the number 3 scores for tibial dyschondroplasia. Ri is an abbreviation for rickets incidence. B.A. is an abbreviation for bone ash. CAR, PR, and PPR represent calcium retention, phosphorus retention and phytate phosphorus retention respectively.

Analysis of Experiment 3 Results

The addition of 1,25-(OH)$_2$D$_3$ (2) to the diet caused an increase in the utilization of phytate phosphorus by the broiler chickens which was apparent from growth, bone ash, blood calcium, and total phosphorus retention. The addition of 1,25-(OH)$_2$D$_3$ in the presence of graded levels of phytase resulted in a gradual increase in the phytate phosphorus utilization from 67% when no phytase was present to 89% when 600 units of phytase/kg of feed was present in the diet.

TABLE 5

| | | Effect of 1,25-(OH)$_2$D$_3$ plus graded levels of phytase | | | | | | | | | |
|---|---|---|---|---|---|---|---|---|---|---|---|
| | 9-d | Tibial dyschondroplasia | | | | | Blood plasma | | Survi- | | | |
| Treatments | wt. g | TDI % | TDS | N3 % | Ri % | G:F | B.A. % | Ca mg/kg | Dialyzable P mg/kg | vors % | CAR % | PR | PPR % |
| Basal | 147 | 20 | 2.00 | 6 | 62 | .692 | 23.7 | 9.83 | 4.70 | 16/20 | 30.87 | 41.58 | 48.63 |
| 37.5 units Phytase | 172 | 19 | 1.00 | 0 | 32 | .724 | 26.6 | 11.83 | 2.50 | 16/20 | 36.28 | 43.61 | 66.38 |
| 75 units Phytase | 161 | 0 | .00 | 0 | 60 | .715 | 23.3 | 12.10 | 1.70 | 20/20 | 26.60 | 37.88 | 49.68 |
| 150 units Phytase | 182 | 10 | .75 | 0 | 70 | .768 | 24.0 | 13.57 | .75 | 20/20 | 17.63 | 33.92 | 52.01 |
| 300 units Phytase | 182 | 5 | .50 | 0 | 60 | .789 | 24.3 | 12.63 | 1.20 | 20/20 | 17.83 | 42.39 | 54.15 |
| 600 units Phytase | 185 | 0 | .00 | 0 | 30 | .764 | 26.4 | 13.38 | .85 | 20/20 | 19.83 | 47.08 | 73.31 |
| Basal + 5 μg 1,25-(OH)$_2$D$_3$ | 187 | 10 | .50 | 0 | 40 | .808 | 26.9 | 14.30 | 1.15 | 18/20 | 31.14 | 55.89 | 66.59 |
| 37.5 Phytase + 5 μg 1,25-(OH)$_2$D$_3$ | 184 | 15 | 2.00 | 5 | 25 | .773 | 29.9 | 14.92 | .95 | 20/20 | 37.28 | 57.03 | 79.11 |
| 75 Phytase + 5 μg 1,25-(OH)$_2$D$_3$ | 181 | 0 | .00 | 0 | 25 | .776 | 28.7 | 13.60 | 1.70 | 20/20 | 35.73 | 57.74 | 80.07 |
| 150 Phytase + 5 μg 1,25-(OH)$_2$D$_3$ | 189 | 6 | .50 | 0 | 36 | .752 | 28.4 | 14.43 | .95 | 19/20 | 34.91 | 56.90 | 84.09 |
| 300 Phytase + 5 μg 1,25-(OH)$_2$D$_3$ | 194 | 25 | 2.00 | 5 | 20 | .788 | 30.1 | 12.99 | .78 | 20/20 | 42.87 | 61.41 | 84.89 |

TABLE 5-continued

| | | Effect of 1,25-(OH)$_2$D$_3$ plus graded levels of phytase | | | | | | | | | | |
|---|---|---|---|---|---|---|---|---|---|---|---|---|
| | 9-d | Tibial dyschondroplasia | | | | | Blood plasma | | Survi- | | | |
| Treatments | wt. g | TDI % | TDS | N3 % | Ri % | G:F | B.A. % | Ca mg/kg | Dialyzable P mg/kg | vors % | CAR % | PR | PPR % |
| 600 Phytase + 5 μg 1,25-(OH)$_2$D$_3$ | 187 | 21 | 1.00 | 0 | 11 | .766 | 32.5 | 14.50 | 1.75 | 19/20 | 44.09 | 61.25 | 88.74 |
| Mean ± SEM | 179 ± 4 | 11 ± 7 | .85 ± .60 | 1 ± 3 | 39 ± 10 | .760 ± .015 | 27.1 ± .7 | 13.2 ± 1.0 | 1.58 ± .64 | | 31.25 ± 4.89 | 49.71 ± 3.77 | 68.97 ± 7.90 |

Experiment 4

The objective of experiment 4 was to determine if the addition of 1,25-(OH)$_2$D$_3$ to a corn-soybean diet containing 0.6% calcium would enhance the utilization of phytate phosphorus in the presence of various levels of phosphate.

Each of the twelve different dietary treatments set forth below were provided to three pens containing ten birds per pen.

1. One diet was a basal diet lacking supplemental inorganic phosphorus, phytase or 1,25-(OH)$_2$D$_3$ (2).
2. Two diets contained graded levels of phosphorus (0.1 and 0.2%) from reagent grade Na$_2$HPO$_4$H$_2$O.
3. One diet contained basal phosphate plus 150 units of phytase.
4. Two diets contained graded levels of phosphorus (0.1 and 0.2%) plus 150 units of phytase (Sigma Chemical Co., St. Louis, Mo.).
5. One diet contained basal levels of phosphorus plus 5 microgram/kg feed of 1,25-(OH)$_2$D$_3$.
6. Two diets contained graded levels of phosphorus (0.1 and 0.2%) plus 5 microgram/kg feed of 1,25-(OH)$_2$D$_3$.
7. One diet contained basal levels of phosphorus plus phytase plus 5 micrograms/kg 1,25-(OH)$_2$D$_3$.
8. Two diets contained graded levels of phosphorus (0.1 and 0.2%) plus 150 units of phytase plus 5 microgram/kg feed of 1,25-(OH)$_2$D$_3$.

All chickens were fed a corn-soybean diet containing only 0.6% calcium, 0.34% phosphorus, and a vitamin mixture supplying 1100 ICU D$_3$/kg of diet.

The results are shown in Table 6 below.

Analysis of Experiment 4 Results

The addition of inorganic phosphate to the diet decreases phytate phosphorus utilization and decreases the effectiveness of 1,25-(OH)$_2$D$_3$ (2) in increasing phytate phosphorus utilization.

TABLE 6

| | Effect of phosphorus, phytase and 1,25-(OH)$_2$D$_3$ | | | | | | | | |
|---|---|---|---|---|---|---|---|---|---|
| Diets | 9-d wt. g | TDI % | TDS | N3 % | Ri % | RiS | Ri #3 % | G:F | B.A. % | TCa % |
| Basal | 153 | 13 | 1.00 | 6 | 75 | 3.00 | 7 | .693 | 24.3 | 12.33 |
| .1% P | 187 | 0 | 0.00 | 0 | 50 | 3.00 | 50 | .769 | 31.8 | 11.95 |
| .2% P | 202 | 22 | 3.00 | 22 | 35 | 3.00 | 38 | .784 | 34.2 | 10.60 |
| 150 units Phytase conc. | 188 | 10 | 1.00 | 5 | 90 | 3.00 | 90 | .801 | 24.7 | 13.37 |
| .1% P + 150 units Phytase conc. | 193 | 25 | 1.30 | 20 | 30 | 3.00 | 30 | .771 | 32.1 | 10.29 |
| .2% P + 150 units Phytase conc. | 203 | 11 | 1.50 | 11 | 6 | 1.50 | 6 | .804 | 34.8 | 11.13 |
| Basal + 5 μg/kg 1,25-(OH)$_2$D$_3$ | 187 | 0 | 0.00 | 0 | 40 | 3.00 | 40 | .732 | 30.8 | 13.88 |
| .1% P + 5 μg/kg 1,25-(OH)$_2$D$_3$ | 193 | 5 | 1.50 | 5 | 10 | 3.00 | 10 | .795 | 34.3 | 13.23 |
| .2% P + 5 μg/kg 1,25-(OH)$_2$D$_3$ | 198 | 16 | 3.00 | 16 | 15 | 3.00 | 15 | .817 | 35.8 | 11.33 |
| Basal + 150 units Phytase + 5 μg/kg 1,25-(OH)$_2$D$_3$ | 181 | 10 | 3.00 | 10 | 25 | 3.00 | 25 | .743 | 31.6 | 11.98 |
| .1% P + 150 units Phytase + 5 μg/kg 1,25-(OH)$_2$D$_3$ | 199 | 10 | 2.00 | 5 | 5 | 1.50 | 5 | .810 | 35.6 | 11.68 |
| .2% P + 150 units Phytase + 5 μg/kg 1,25-(OH)$_2$D$_3$ | 182 | 0 | 0.00 | 0 | 5 | 1.50 | 5 | .709 | 36.1 | 10.65 |
| Mean ± SEM | 188 ± 6 | 10 ± 10 | 1.44 ± .88 | 8 ± 8 | 32 ± 16 | 2.63 ± .75 | 32 ± 17 | .769 ± .020 | 32.2 ± .8 | 11.87 ± .06 |

| Diets | DP % | Survivors | CAR | PR | PPR |
|---|---|---|---|---|---|
| Basal | 1.22 | 18/20 | 39.02 | 49.04 | 53.89 |
| .1% P | 1.53 | 20/20 | 30.08 | 53.18 | 53.63 |
| .2% P | 4.22 | 19/20 | 53.77 | 54.25 | 48.02 |
| 150 units Phytase conc. | .70 | 20/20 | 35.09 | 50.07 | 63.49 |
| .1% P + 150 units Phytase conc. | 2.74 | 20/20 | 45.17[abc] | 57.48 | 58.86 |
| .2% P + 150 units Phytase conc. | 4.37 | 19/20 | 53.10[ab] | 53.23 | 51.36 |
| Basal + 5 μg/kg 1,25-(OH)$_2$D$_3$ | 1.19 | 20/20 | 48.93[abc] | 65.89 | 79.40 |
| .1% P + 5 μg/kg 1,25-(OH)$_2$D$_3$ | 3.02 | 20/20 | 51.16 | 62.64 | 72.16 |

TABLE 6-continued

| Effect of phosphorus, phytase and 1,25-(OH)₂D₃ | | | | | |
|---|---|---|---|---|---|
| .2% P + 5 μg/kg 1,25-(OH)₂D₃ | 4.73 | 19/20 | 55.69 | 57.72 | 72.66 |
| Basal + 150 units Phytase + 5 μg/kg 1,25-(OH)₂D₃ | 2.43 | 20/20 | 50.17 | 66.11 | 76.64 |
| .1% P + 150 units Phytase + 5 μg/kg 1,25-(OH)₂D₃ | 3.36 | 20/20 | 56.02 | 62.63 | 75.02 |
| .2% P + 150 units Phytase + 5 μg/kg 1,25-(OH)₂D₃ | 4.54 | 20/20 | 54.44 | 49.08 | 63.85 |
| Mean ± SEM | 2.83 ± .45 | | 47.72 ± 5.90 | 56.77 ± 2.63 | 64.08 ± 7.176 |

Experiment 5

The objective of experiment 5 was to determine if the addition of 1,25-(OH)₂D₃ (2) to a corn-soybean meal diet with three levels of calcium with and without added phytase would enhance the utilization of phytate phosphorus.

Each of the twelve different dietary treatments set forth below were provided to three pens containing ten birds per pen.

1. Three diets contained graded levels of calcium (0.40%, 0.57% and 0.72%). The concentration of 0.40% calcium was obtained by adding 17.6 grams limestone per kilograms feed. The concentration of 0.57% calcium was obtained by adding 35.2 g/kg limestone. The 0.72% calcium value was obtained by adding 52.8 g/kg limestone.
2. Three diets contained 75 units phytase per kilogram feed plus each of the graded levels of calcium.
3. Three diets contained 5 microgram/kg feed of 1,25-(OH)₂D₃ plus each of the graded levels of calcium.
4. Three diets contained 5 microgram/kg feed of 1,25-(OH)₂D₃ plus phytase plus the three graded levels of calcium.

All chickens were fed a corn-soybean diet containing the diet specified above and a vitamin mixture supplying 1100 ICU D₃/kg of diet.

The results are shown in Table 7 below.

Analysis of Experiment 5 Results

Feeding the low calcium diet (0.40%) made it possible to obtain a very high level of phytate phosphorus retention (86%) with the basal diet containing no added phytase or 1,25-(OH)₂D₃ (2) to the diet. The addition of phytase or 1,25-(OH)₂D₃ to the diet resulted in slightly greater phytate utilization. However, greater phytate utilization was apparent when both phytase and 1,25-(OH)₂D₃ were added to the diet, especially in the higher dietary calcium levels.

TABLE 7

| Effect of 1,25-(OH)₂D₃ and graded levels of calcium | | | | | | | | | | |
|---|---|---|---|---|---|---|---|---|---|---|
| Treatments | 9-d wt. g | TDI % | TDS | N3 % | Ri % | RiS | Ri #3 % | G:F | B.A. % | TCa % |
| 0.40% Calcium | 177 | 5 | 1.50 | 5 | 90 | 3.00 | 90 | .765 | 28.1 | 8.18 |
| 0.57% Calcium | 207 | 15 | 1.50 | 5 | 90 | 2.11 | 50 | .806 | 32.8 | 9.43 |
| 0.72% Calcium | 192 | 15 | 1.25 | 5 | 65 | 1.91 | 30 | .780 | 34.2 | 10.60 |
| 0.40% Calcium + Phytase | 189 | 5 | 1.50 | 5 | 95 | 2.80 | 85 | .825 | 28.5 | 8.63 |
| 0.57% Calcium + Phytase | 201 | 15 | 3.00 | 15 | 60 | 2.12 | 35 | .827 | 33.3 | 9.88 |
| 0.72% Calcium + Phytase | 200 | 37 | 2.42 | 26 | 64 | 2.75 | 53 | .797 | 35.7 | 11.25 |
| 0.40% Calcium + 1,25-(OH)₂D₃ | 185 | 15 | 1.50 | 5 | 75 | 2.45 | 55 | .732 | 30.9 | 9.33 |
| 0.57% Calcium + 1,25-(OH)₂D₃ | 211 | 21 | 2.25 | 16 | 70 | 2.40 | 42 | .831 | 34.8 | 10.58 |
| 1.89% Calcium[1] + 1,25-(OH)₂D₃ | 160 | 0 | 0.00 | 0 | 16 | 1.50 | 6 | .759 | 34.1 | 13.30 |
| 0.40% Calcium + 1,25-(OH)₂D₃ + Phytase | 190 | 20 | 2.50 | 15 | 85 | 2.75 | 75 | .764 | 31.1 | 9.73 |
| 0.57% Calcium + 1,25-(OH)₂D₃ + Phytase | 185 | 15 | 0.50 | 0 | 70 | 1.25 | 10 | .716 | 35.3 | 10.35 |
| 0.72% Calcium + 1,25-(OH)₂D₃ + Phytase | 191 | 22 | 2.00 | 11 | 28 | 1.84 | 11 | .786 | 36.7 | 11.10 |
| Mean ± SEM | 191 ± 7 | 15 ± 6 | 1.66 ± .72 | 9 ± 4 | 67 ± 9 | 2.24 ± .26 | 45 ± 9 | .782 ± .029 | 33.0 ± .6 | 10.20 ± .71 |

| Treatments | DP % | Survivors | CAR % | PR % | PPR % |
|---|---|---|---|---|---|
| 0.40% Calcium | 7.90 | 19/20 | 68.61 | 37.66 | 86.21 |
| 0.57% Calcium | 8.15 | 19/20 | 60.57 | 49.07 | 78.39 |
| 0.72% Calcium | 4.70 | 20/20 | 51.51 | 52.01 | 55.16 |
| 0.40% Calcium + Phytase | 9.30 | 20/20 | 62.27 | 46.34 | 89.37 |
| 0.57% Calcium + Phytase | 7.10 | 20/20 | 58.79 | 52.56 | 69.95 |
| 0.72% Calcium + Phytase | 6.95 | 19/20 | 52.40 | 54.84 | 63.38 |
| 0.40% Calcium + 1,25-(OH)₂D₃ | 7.45 | 20/20 | 64.53 | 39.67 | 94.42 |
| 0.57% Calcium + 1,25-(OH)₂D₃ | 7.30 | 19/20 | 64.07 | 53.27 | 78.67 |
| 1.89% Calcium[1] + | 4.60 | 19/20 | 50.40 | 47.46 | 37.84 |

TABLE 7-continued

| Effect of 1,25-$(OH)_2D_3$ and graded levels of calcium | | | | | |
|---|---|---|---|---|---|
| 1,25-$(OH)_2D_3$ | | | | | |
| 0.40% Calcium + 1,25-$(OH)_2D_3$ + Phytase | 7.70 | 20/20 | 71.88 | 40.91 | 90.87 |
| 0.57% Calcium + 1,25-$(OH)_2D_3$ + Phytase | 8.25 | 20/20 | 59.73 | 44.49 | 96.70 |
| 0.72% Calcium + 1,25-$(OH)_2D_3$ + Phytase | 7.90 | 20/20 | 63.00 | 56.63 | 75.51 |
| Mean ± SEM | 7.28 ± .80 | | 60.64 ± 2.52 | 48.07 ± 3.90 | 76.20 ± 2.74 |

[1]There was a mixing error in preparing the diet that should have contained 0.72% calcium and 1,25-$(OH)_2D_3$. The diet mixed and fed actually contained 1.89% calcium.

Experiment 6

The objective of experiment 6 was to determine if the addition of the vitamin $D_3$ derivatives 1,25-$(OH)_2D_3$ (2), 1-$OHD_3$ (4) or 24,25-$(OH)_2D_3$ (8) to a corn-soybean meal diet with and without added phytase would enhance the utilization of phytate phosphorus.

Each of the eight different dietary treatments set forth below were provided to two pens containing ten birds per pen.
1. One diet contained basal levels of phytase.
2. One diet contained 150 units of phytase.
3. Three diets contained 5 micrograms/kg of either 1,25-$(OH)_2D_3$ (2), 1-$OHD_3$ (4), or 24,25-$(OH)_2D_3$ (8).
4. Three diets contained 150 units of phytase plus 5 micrograms/kg of either 1,25-$(OH)_2D_3$ (2), 1-$OHD_3$ (4), or 24,25-$(OH)_2D_3$ (8).

All chickens were fed a corn-soybean diet containing the diet specified above and a vitamin mixture supplying 1100 ICU $D_3$/kg of diet.

The results are shown in Table 8 below.

Analysis of Experiment 6 Results

The 1,25-$(OH)_2D_3$ (2) and 1-$OHD_3$ (4) supplementation of the diet resulted in increased nine-day weights and bone ash as contrasted to supplementation with 24,2-$(OH)_2D_3$ (8) which had no effect on these criteria in the presence or absence of supplemental phytase. In this study, the 1-$OHD_3$(4) and 24,25-$(OH)_2D_3$ (8) did not appear to increase phytate phosphorus utilization in the absence of phytase. Supplementation with 1,25-$(OH)_2D_3$ (2) increased phytate phosphorus utilization in the presence or absence of phytase.

TABLE 8

Effects of 1,25-$(OH)_2D_3$, 1-$OHD_3$, and 24,25-$(OH)_2D_3$

| Treatments | 9-d wt. g | TDI % | TDS | TD N3 | Ri I % | Ri S | Ri #3 | G:F | B.A. % | TCa % | DP % | CAR | PR | PPR |
|---|---|---|---|---|---|---|---|---|---|---|---|---|---|---|
| Basal | 143 | 7 | 1.33 | 3 | 86 | 3.00 | 86 | .655 | 24.3 | 11.92 | 1.63 | 40.29 | 49.18 | 61.11 |
| 150 Phytase | 159 | 8 | 1.33 | 4 | 82 | 3.00 | 79 | .685 | 24.9 | 13.25 | .54 | 37.49 | 47.47 | 57.18 |
| 150 Phytase + 1,25-$(OH)_2D_3$ | 166 | 17 | 1.11 | 7 | 53 | 3.00 | 53 | .704 | 29.6 | 15.63 | 1.27 | 40.53 | 62.28 | 80.29 |
| 150 Phytase + 1-$OHD_3$ | 168 | 17 | 2.11 | 7 | 58 | 3.00 | 59 | .741 | 28.1 | 14.47 | .67 | 41.76 | 53.61 | 69.37 |
| 150 Phytase + 24,25-$(OH)_2D_3$ | 152 | 7 | .67 | 4 | 75 | 3.00 | 82 | .716 | 24.3 | 11.77 | 2.07 | 33.32 | 47.05 | 69.17 |
| 1,25-$(OH)_2D_3$ | 168 | 4 | 1.00 | 4 | 24 | 3.00 | 25 | .705 | 31.7 | 12.50 | 1.93 | 54.57 | 65.27 | 72.93 |
| 1-$OHD_3$ | 160 | 10 | .67 | 0 | 77 | 3.00 | 77 | .718 | 26.1 | 14.77 | .86 | 37.15 | 49.67 | 61.29 |
| 24,25-$(OH)_2D_3$ | 150 | 4 | 1.00 | 4 | 72 | 3.00 | 71 | .707 | 23.5 | 14.84 | .61 | 30.99 | 49.65 | 62.45 |
| Mean ± SEM | 158 ± 4 | 9 ± 6 | 1.11 ± .80 | 4 ± 4 | 66 ± 8 | 3.00 ± 0 | 66 ± 8 | .704 ± .023 | 26.6 ± .4 | 13.61 ± .89 | 1.20 ± .39 | 39.57 ± 2.44 | 53.21 ± 2.41 | 67.07 ± 7.74 |

Experiment 7

The objective of experiment 7 was to determine if the addition of the vitamin $D_3$ derivatives 1,24,25-$(OH)_3D_3$ (5), 1,25-$(OH)$-24-$FD_3$ (6), or 1,25-$(OH)_2$-26,27$[^3H]_6D_3$ (3) to a corn-soybean meal diet with and without added phytase would enhance the utilization of phytate phosphorus.

Each of the eight different dietary treatments set forth below were provided to two pens containing ten birds per pen.
1. One diet contained basal levels of phytase and vitamin $D_3$ derivatives.
2. One diet contained 150 units of phytase.
3. Three diets contained 5 micrograms/kg of either 1,24,25$(OH)_3D_3$ (5), 1,25-$(OH)_2$-24-$FD_3$ (6) or 1,25-$(OH)_2$-26,27$[^3H]_6D_3$ (3).
4. Three diets contained 150 units of phytase plus 5 micrograms/kg of either 1,24,25-$(OH)_3D_3$ (5), 1,25-$(OH)_2$-24-$FD_3$(6) or 1,25-$(OH)_2$-26,27$[^3H]_6D_3$ (3).

All chickens were fed a corn-soybean diet containing the diet specified above and a vitamin mixture supplying 1100 ICU D/kg of diet.

The results are shown in Table 9 below.

Analysis of Experiment 7 Results

All three of the $D_3$ derivatives increased the utilization of phytate phosphorus by the broiler chickens, but 1,25-(OH)$_2$-26,27[$^3$H]$_6$D$_3$ (3) was more effective than the other two vitamin D$_3$ derivatives.

for Measuring $^{65}$Zn Absorption and Biological Half-life in the Chicken," Poult. Sci. 47:991–999 (1968). Specifi-

TABLE 9

Effects of 1,24,25-(OH)$_3$D$_3$, 1,25-(OH)$_2$-24-FD$_3$, and 1,25-(OH)$_2$-26,27[$^3$H]$_6$D$_3$

| Treatments | 9-d wt. g | TDI % | TDS | TD N3 | RiI % | RiS | Ri #3 | G:F | B.A. % | TCa % | DP % | CAR | PR | PPR |
|---|---|---|---|---|---|---|---|---|---|---|---|---|---|---|
| Basal | 155 | 10 | 1.00 | 3 | 53 | 2.90 | 50 | .703 | 25.79 | 10.38 | 1.37 | 40.12 | 46.32 | 53.11 |
| 150 units Phytase | 158 | 10 | 1.00 | 0 | 73 | 3.00 | 73 | .728 | 24.19 | 10.92 | .31 | 39.73 | 53.96 | 63.61 |
| Phytase + 1,24,25-(OH)$_3$D$_3$ | 168 | 7 | .66 | 0 | 90 | 2.92 | 87 | .750 | 25.78 | 11.18 | .21 | 43.65 | 55.93 | 64.53 |
| Phytase + 1,25-(OH)$_2$-24R-FD$_3$ | 161 | 18 | 1.00 | 0 | 65 | 2.89 | 61 | .700 | 27.04 | 10.67 | .64 | 44.66 | 56.98 | 66.85 |
| Phytase + 1,25-(OH)$_2$-26,27[$^3$H]$_6$D$_3$ | 169 | 7 | .33 | 0 | 37 | 3.00 | 37 | .749 | 31.00 | 10.55 | 2.40 | 50.65 | 70.09 | 81.47 |
| 1,24,25-(OH)$_3$D$_3$ | 151 | 7 | .33 | 0 | 79 | 2.93 | 76 | .680 | 26.27 | 10.58 | .44 | 46.90 | 54.68 | 67.71 |
| 1,25-(OH)$_2$-24R-FD$_3$ | 162 | 18 | 1.66 | 4 | 72 | 3.00 | 72 | .737 | 27.78 | 10.68 | .74 | 47.36 | 53.39 | 63.12 |
| 1,25-(OH)$_2$-26,27[$^3$H]$_6$D$_3$ | 160 | 3 | .33 | 0 | 30 | 3.00 | 30 | .716 | 30.25 | 10.12 | 1.57 | 48.87 | 62.08 | 77.03 |
| Mean ± SEM | 160 ± 5 | 10 ± .6 | .83 ± .41 | 1 ± 2 | 63 ± 9 | 2.95 ± .07 | 61 ± 9 | .720 ± .017 | 27.26 ± .64 | 10.64 ± .64 | .96 ± .40 | 45.24 ± 3.54 | 56.68 ± 2.30 | 67.18 ± 4.19 |

Example 2

Treatment of Tibial Dyschondroplasia with Vitamin D$_3$ Derivatives

The effectiveness of 1,25-dihydroxycholecalciferol (2), 1,25-dihydroxy-26,27-hexadeuterocholecalciferol (3), 1hydroxycholecalciferol (4), 1,24,25-trihydroxycholecalciferol (5), and 1,25-dihydroxy-24-fluorocholecalciferol (6) in reducing the incidence of tibial dyschondroplasia in chickens has been demonstrated using the following experimental procedures.

Newly hatched Peterson X Arbor Acre cockerels obtained from a commercial hatchery were housed as described in Example 1 above. The basal diet used is described above in Table 2. Disulfiram was added to the basal diet of some chickens as indicated in Table 10 at a level of 30 mg/kg of feed. The following levels of vitamin D$_3$ and its metabolites were added to the diet as indicated in Tables 10 and 11:

Vitamin D$_3$, 27.5 micrograms per kilogram of feed (1100 ICU/kilogram); and 1,25-dihydroxycholecalciferol (2), 1,25-dihydroxy-26,27hexadeuterocholecalciferol (3), 1-hydroxycholecalciferol (4), 1,24(R), 25-trihydroxycholecalciferol (5), 1,25-dihydroxy-24(R)-fluorocholecalciferol (6), and 25-hydroxycholecalciferol (7) at 10 micrograms per kilogram.

At 16 days of age, pen body weights were obtained for all birds and their feed consumption was recorded. The birds were then sacrificed and examined at random for tibial dyschondroplasia by making a longitudinal cut across the tibia and scoring for incidence and severity of tibial dyschondroplasia as described in Example 1 above. After the tibia was scored for incidence and severity of tibial dyschondroplasia, the left tibia was removed for a bone ash determination on the fat-free dried bone.

Absorption and retention of dietary calcium was measured by orally dosing chicks with $^{47}$Ca and then measuring the total body radioactive count, as described in Suso and Edwards, "A Study of Techniques cally, ten seven day old birds in one pen under the indicated dietary treatments were dosed orally with 0.5 milliliter of water solution containing 0.5 microcuries of $^{47}$Ca and 0.1 to 1.0 micrograms of calcium. The total body radioactive content of the individual chickens was determined immediately following dosing, and also on days 7, 9, 12 and 14 following dosing. A plot of percent administered $^{47}$Ca which was retained versus number of days yields a line which has a slope corresponding to the half-life of the radioactive calcium in the chicken, and a y-intercept that corresponds to the amount of calcium absorbed by the chicken.

Effect of vitamin D derivatives on Tibial Dyschodroplasia.

The effect in broiler cockerels of vitamin D$_3$ (1), 25-hydroxycholecalciferol (1), and 1,25-dihydroxycholecalciferol (2) on growth, feed efficiency, bone ash, $^{47}$Ca retention, and incidence and severity of tibial dyschondroplasia was determined in Studies 1 and 2. The results are shown in Table 10 below. The basal diet contained 1100 ICU (27.5 micrograms) vitamin D$_3$ per kilogram feed. Disulfiram was added as indicated to the diets of some chickens to increase the incidence of the disease in order to further measure the effectiveness of the compounds.

As shown below in Table 10, 1,25-dihydroxycholecalciferol (2), in the presence or absence of disulfiram, reduced the incidence and severity of tibial dyschondroplasia over the basal diet, and increased bone ash. 25-(OH)-Cholecalciferol (7), in the presence or absence of disulfiram, also reduced the incidence of tibial dyschondroplasia over the basal diet. Further, a diet with 1,25-dihydroxycholecalciferol resulted in significantly more dietary $^{47}$Ca absorbed than in a basal diet, while increasing the half-life, or retention, of the calcium administered.

Table 11, shown below, illustrates the results of Studies 3 and 4, in which the effect of vitamin D (choiecalciferol) (1), 1,25-dihydroxycholecalciferol (2), 1,25- dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), and 24,25-dihydroxycholecalciferol (8), on the incidence and severity of tibial dyschondroplasia, bone ash and absorption and retention of calcium was measured. The basal diet contained 1100 ICU of vitamin $D_3$ per kilogram feed.

In Tables 10 and 11, values with different superscript letters are significantly different, $P \leq 0.5$.

Studies 3 and 4 substantiated the results of studies 1 and 2 that administration of 10 microgram/kg feed of 1,25-dihydroxycholecalciferol (2) to the bird per day for the life of the bird substantially reduces the incidence and severity of tibial dyschondroplasia over the basal diet, and increases bone ash.

The addition of 24,25-dihydroxycholecalciferol (8) was not effective in preventing the development of tibial dyschondroplasia.

The chickens that received feed containing 1,24,25-trihydroxycholecalciferol (5), 1-hydroxycholecalciferol (4), 1,25-dihydroxy-26,27-hexadeuterocholecalciferol (3) and 1,25-dihydroxy-24-fluorocholecalciferol (6) had a significant reduction in the incidence of tibial dyschondroplasia.

TABLE 10

Effect of Vitamin $D_3$; 25-$OHD_3$ and 1,25-$(OH)_2D_3$ on Severity of Tibial Dyschondroplasia With and Without Disulfiram

| Treatments | 16 Day wt | Gain:Feed | Bone ash | Tibial Dyschondroplasia Incidence | Score | #3/total | $^{47}Ca$ Intercept | Slope |
|---|---|---|---|---|---|---|---|---|
| Study 1 | | | | | | | | |
| Basal | 416 | .696 | 40.6 | 42 | 2.77 | 10/30 | | |
| Basal + $D_3$ | 451 | .734 | 40.4 | 26 | 2.38 | 4/27 | | |
| Basal + 25-$OHD_3$ | 395 | .667 | 40.2 | 17 | 1.50 | 1/28 | | |
| Basal + 1,25-$(OH)_2D_3$ | 421 | .670 | 42.5 | 13 | 1.75 | 1/29 | | |
| Disulfiram | 433 | .750 | 39.9 | 70 | 2.71 | 16/30 | | |
| Disulfiram + $D_3$ | 432 | .708 | 40.0 | 40 | 2.80 | 9/27 | | |
| Disulfiram + 25-$OHD_3$ | 398 | .706 | 39.7 | 58 | 2.54 | 11/30 | | |
| Disulfiram + 1,25-$(OH)_2D_3$ | 426 | .701 | 41.9 | 23 | 2.33 | 4/30 | | |
| Means ± SEM | 420 ± 13 | .704 | .032 | 40.6 ± .2 | 36 ± 9 | 2.11 ± .48 | | |
| Study 2 | | | | | | | | |
| Basal | 375 | .707 | 40.5 | 39 | 1.94 | 6/29 | 72 | −1.60 |
| Basal + $D_3$ | 368 | .647 | 40.5 | 31 | 2.47 | 5/29 | 77 | −1.88 |
| Basal + 25$OHD_3$ | 392 | .713 | 40.6 | 27 | 2.78 | 7/30 | 72 | −1.59 |
| Basal + 1,25$(OH)_2D_3$ | 361 | .661 | 42.2 | 13 | 2.17 | 2/30 | 84 | −2.85 |
| Disulfiram | 394 | .671 | 40.3 | 65 | 2.76 | 14/28 | 73 | −1.59 |
| Disulfiram +$D_3$ | 374 | .666 | 40.3 | 51 | 2.74 | 12/30 | 72 | −1.97 |
| Disulfiram + 25$OHD_3$ | 395 | .728 | 40.5 | 49 | 2.76 | 11/28 | 74 | −1.67 |
| Disulfiram + 1,25$(OH)_2D_3$ | 377 | .684 | 42.0 | 30 | 2.44 | 6/30 | 79 | −2.11 |
| Means ± SEM | 380 ± 12 | .685 ± .026 | 40.8 ± .3 | 38 ± 9 | 2.51 ± .31 | | 75 ± 3 | −1.91 ± .29 |

TABLE 11

Effect of Vitamin D3 and Vitamin D3 Derivatives on Severity of Tibial Dyschondroplasia

Study 3

| Vit D Compound | 16 Day Wt. | Gain/Feed | Tibial Dyschondroplasia Incidence | Score | #3/No. | % N3 | % N2 + 3 | $Ca^{47}$ Ret. | Slope |
|---|---|---|---|---|---|---|---|---|---|
| none | 421 | .711$^a$ | 63 | 1.85 | 11/60 | 18 | 37 | 70$^{bc}$ | −1.01$^b$ |
| $D_3$ | 434 | .709$^a$ | 82 | 1.69 | 13/59 | 22 | 34 | 75$^{abc}$ | −1.13$^b$ |
| 1,25$(OH)_2D_3$ | 421 | .66$^b$ | 56 | 1.48 | 5/58 | 9 | 16 | 78$^{ab}$ | −.72$^{ab}$ |
| 24,25$(OH)_2D_3$ | 424 | .696$^{ab}$ | 78 | 2.03 | 17/59 | 29 | 53 | 67$^c$ | −.77$^{ab}$ |
| 1,24,25$(OH)_2D_3$ | 428 | .688$^{ab}$ | 57 | 1.58 | 6/60 | 10 | 22 | 76$^{abc}$ | −.77$^{ab}$ |
| 1-$OHD_3$ | 423 | .661$^b$ | 42 | 1.51 | 3/60 | 5 | 17 | 75$^{abc}$ | −.95$^b$ |
| 1,25$(OH)_2$-26-27$[^2H]_6D_3$ | 422 | .687$^{ab}$ | 42 | 1.30 | 0/60 | 0 | 8 | 80$^a$ | .15$^a$ |
| 1,25$(OH)_2$-24R-$FD_3$ | 413 | .663$^b$ | 60 | 1.36 | 3/60 | 5 | 15 | 72$^{abc}$ | −.47$^{ab}$ |
| Mean ± SEM | 423 ± 7 | .685 ± 0.13 | 59 ± 7 | 1.60 ± 15 | | 12 ± 4.5 | | 74 ± 3 | −.71 ± .31 |

Study 4

| Vit. D Compound | 16 Day wt. | Gain/feed | Bone ash | Tibial Dyschondroplasia Incidence | Score | % #3 | #3/Total |
|---|---|---|---|---|---|---|---|
| None (basal diet) | 356$^{cd1}$ | .681$^{ab}$ | 35.07$^c$ | 54$^a$ | 2.30$^{ab}$ | 35$^a$ | 19/55 |
| $D_3$ | 383$^a$ | .701$^a$ | 35.68$^{bc}$ | 44$^{ab}$ | 2.75$^a$ | 35$^a$ | 20/58 |
| 1,25$(OH)_2D_3$ | 355$^{cd}$ | .652$^b$ | 36.88$^a$ | 18$^d$ | 1.58$^b$ | 8$^b$ | 4/52 |
| 24,25$(OH)_2D_3$ | 351$^d$ | .663$^b$ | 35.53$^{bc}$ | 53$^a$ | 2.78$^a$ | 46$^a$ | 25/56 |
| 1,24,25$(OH)_2D_3$ | 376$^{ab}$ | .681$^{ab}$ | 36.07$^b$ | 23$^{cd}$ | 1.89$^{ab}$ | 14$^b$ | 8/57 |
| 1$OHD_3$ | 372$^{abc}$ | .655$^b$ | 36.77$^a$ | 29$^{bcd}$ | 2.21$^{ab}$ | 15$^b$ | 8/57 |
| 1,25$(OH)_2$-26-27$[^2H]_6D_3$ | 360$^{bcd}$ | .646$^b$ | 37.45$^a$ | 16$^d$ | 1.63$^b$ | 7$^b$ | 4/58 |
| 1,25$(OH)_2$-24R-$FD_3$ | 360$^{bcd}$ | .661$^b$ | 35.48$^{bc}$ | 41$^{abc}$ | 2.06$^{ab}$ | 16$^b$ | 9/56 |
| Mean ± SEM | 364 ± 6 | .667 ± .012 | 36.12 ± .23 | 34 ± 6 | 2.15 ± .31 | 22 ± 5 | |

Modifications and variations of the present methods and compositions for enhancement of phytate phosphorus utilization and prevention or treatment of tibial dyschondroplasia will be obvious to those skilled in the art from the foregoing detailed description. Such modifications and variations are intended to come within the scope of the appended claims.

I claim:

1. An animal feed composition comprising a vitamin $D_3$ derivative selected from the group consisting of 1,25-dihydroxycholecalciferol; 1,25-dihydroxy-26,27-hexadeuterocholecalciferol; 1-hydroxycholecalciferol; 1,24,25-trihydroxycholecalciferol; and 1,25-dihydroxy-24-fluorocholecalciferol; 25-hydroxycholecalciferol; and mixtures thereof in combination with an animal feed for growing animals, wherein the concentration of vitamin $D_3$ derivative is between 1 and 10 micrograms per kilogram feed for growing animals, and is in an amount effectively inhibiting development of tibial dyschondroplasia in growing animals ingesting the feed.

2. The composition of claim 1 wherein the concentration of vitamin $D_3$ derivative is between 3 and 6 micrograms per kilogram feed.

3. The composition of claim 2 wherein the concentration of vitamin $D_3$ derivative is approximately 5 micrograms per kilogram feed.

4. The composition of claim 1 wherein the animal feed has a calcium content of between 0.5 and 1.3% by weight.

5. The composition of claim 4 wherein the animal feed has a phosphorous content of between 0.4 and 0.9% by weight.

6. The composition of claim 1 further comprising active phytase.

7. The composition of claim 6 comprising an amount of phytase between 30 and 600 units per kilogram feed.

8. The composition of claim 1 wherein the animal feed is selected from the group consisting of poultry feed and swine feed.

9. A method of preparing an animal feed composition comprising the steps of adding to an animal feed for a growing animal a vitamin $D_3$ derivative selected from the group consisting of 1,25-dihydroxycholecalciferol; 1,25-dihydroxy-26,27-hexadeutero-cholecalciferol; 1-hydroxycholecalciferol; 1,24,25-trihydroxycholecalciferol; and 1,25-dihydroxy-24-fluorocholecalciferol; 25-hydroxycholecalciferol; and mixtures thereof, wherein the concentration of vitamin $D_3$ derivative is added to between 1 and 10 micrograms per kilogram feed for growing animals, and is in an amount effectively inhibiting development of tibial dyschondroplasia in growing animals ingesting the feed.

10. The method of claim 9 wherein the animal feed has a calcium concentration of between 0.5 and 1.3% by weight.

11. The method of claim 10 wherein the animal feed has a phosphorus concentration of between 0.4 and 0.9% by weight.

12. The method of claim 9 further comprising adding active phytase to the feed.

13. The animal feed composition of claim 4 wherein the animals are poultry animals.

14. The animal feed composition of claim 13 wherein the animals are broilers.

15. The method of claim 10 wherein the animals are poultry animals.

16. The method of claim 15 wherein the animals are broilers.

17. An animal feed composition comprising a vitamin $D_3$ derivative selected from the group consisting of 1,25-dihydroxycholecalciferol; 1,25-dihydroxy-26,27-hexadeuterocholecalciferol; 1-hydroxycholecalciferol; 1,24,25-trihydroxycholecalciferol; and 1,25-dihydroxy-24-fluorocholecalciferol; 25-hydroxycholecalciferol; and mixtures thereof in combination with an animal feed and active phytase.

18. The feed composition of claim 17 wherein the phytase is in an amount between 30 and 600 units per kilogram of feed.

19. A method of preparing an animal feed composition comprising the steps of adding to an animal feed a vitamin $D_3$ derivative selected from the group consisting of 1,25-dihydroxycholecalciferol; 1,25-dihydroxy-26,27-hexadeuterocholecalciferol; 1-hydroxycholecalciferol; 1,24,25-trihydroxycholecalciferol; and 1,25-dihydroxy-24-fluorocholecalciferol; 25-hydroxycholecalciferol; and mixtures thereof in combination with active phytase.

20. The method of claim 19 wherein the phytase is in an amount between 30 and 600 units per kilogram of feed.

* * * * *